(12) United States Patent
Roberts et al.

(10) Patent No.: US 10,717,099 B2
(45) Date of Patent: Jul. 21, 2020

(54) SYSTEM AND METHOD FOR MARKING BALES OF HAY BASED ON PARAMETERS COLLECTED DURING BALING

(71) Applicants: Jeffrey S. Roberts, Hudson, WI (US); Blake Holt, Enterprise, UT (US)

(72) Inventors: Jeffrey S. Roberts, Hudson, WI (US); Blake Holt, Enterprise, UT (US)

(73) Assignee: Harvest Tec Incorporated, Hudson, WI (US)

( * ) Notice: Subject to any disclaimer, the term of this patent is extended or adjusted under 35 U.S.C. 154(b) by 52 days.

(21) Appl. No.: 14/544,718

(22) Filed: Feb. 9, 2015

(65) Prior Publication Data

US 2018/0021796 A1  Jan. 25, 2018

(51) Int. Cl.
| | |
|---|---|
| *B05B 12/12* | (2006.01) |
| *G01N 33/02* | (2006.01) |
| *B05B 9/04* | (2006.01) |
| *B05B 12/14* | (2006.01) |
| *A01F 15/08* | (2006.01) |

(52) U.S. Cl.
CPC .............. *B05B 12/12* (2013.01); *A01F 15/08* (2013.01); *B05B 9/0406* (2013.01); *B05B 9/0423* (2013.01); *B05B 12/1472* (2013.01); *G01N 33/02* (2013.01); *A01F 2015/0891* (2013.01)

(58) Field of Classification Search
None
See application file for complete search history.

(56) References Cited

U.S. PATENT DOCUMENTS

| | | | |
|---|---|---|---|
| 7,093,406 B2 * | 8/2006 | Anstey ................ | A01F 15/0715 206/83.5 |
| 2005/0210699 A1 * | 9/2005 | Philippe .................. | A01F 25/08 34/191 |
| 2007/0175341 A1 * | 8/2007 | Roberts ................... | A01F 15/08 100/102 |

* cited by examiner

*Primary Examiner* — Nathan T Leong
(74) *Attorney, Agent, or Firm* — Skinner and Associates, Inc.; Joel D. Skinner, Jr.

(57) ABSTRACT

Variable marks are applied to the outside of bales of hay that assign each bale to a group based on pre-selected parameters collected during baling.

10 Claims, 2 Drawing Sheets

SYSTEM AND METHOD FOR MARKING BALES OF HAY BASED ON PARAMETERS COLLECTED DURING BALING

CROSS REFERENCE TO RELATED APPLICATIONS

This application is a related to:

U.S. application Ser. No. 13/573,461, A method for Calculating Feed Value of Alfalfa Hay Using Information Available at Time of Baling filed Sep. 17, 2012.

A System and method for identifying bales of hay, U.S. Pat. No. 7,415,924 B2.

A System and Method for Identifying Bales of Hay, U.S. Pat. No. 7,621,111 B2.

THE NAMES OF PARTIES ON A JOINT RESEARCH AGREEMENT

Not Applicable.

STATEMENT REGARDING FEDERALLY SPONSORED RESEARCH FOR DEVELOPMENT

Not Applicable.

BACKGROUND

The primary use of hay that is packaged by a baling implement is to feed livestock. Hay is cut, sometimes raked or otherwise manipulated, and then can be packaged with a baling implement. Each individual bale has different values of feeding quality even though multiple bales can appear the same especially when viewed from the exterior of the bale. The differences in feeding quality for each bale are a result of variation in multiple factors, most notably, the properties of the crop before it is cut, the moisture of the hay as it is baled, the duration between cutting and harvesting and the effect of later manipulation on the windrow. These factors can be measured during the baling process by methods such as sensing position of the baler in the field as it is baling, recording the time and date of baling, determining moisture with sensors mounted in the baler, and density calculations of the bale that indicates the feed quality of the bale as disclosed by Roberts in A method for Calculating Feed Value of Alfalfa Hay Using Information Available at Time of Baling. In the system and method that has been invented, factors affecting feed quality are measured at time of baling, values are grouped by a processor and exterior markings are applied to each bale based on the group the measured value places the bale in.

BRIEF DESCRIPTION OF THE INVENTION

A device to apply multiple variations of exterior markings to bales of hay receives commands from a processor that determines which variation to apply based on inputs from sensors reading values of the bale being marked.

DETAILED DESCRIPTION OF THE INVENTION

Figure 1:
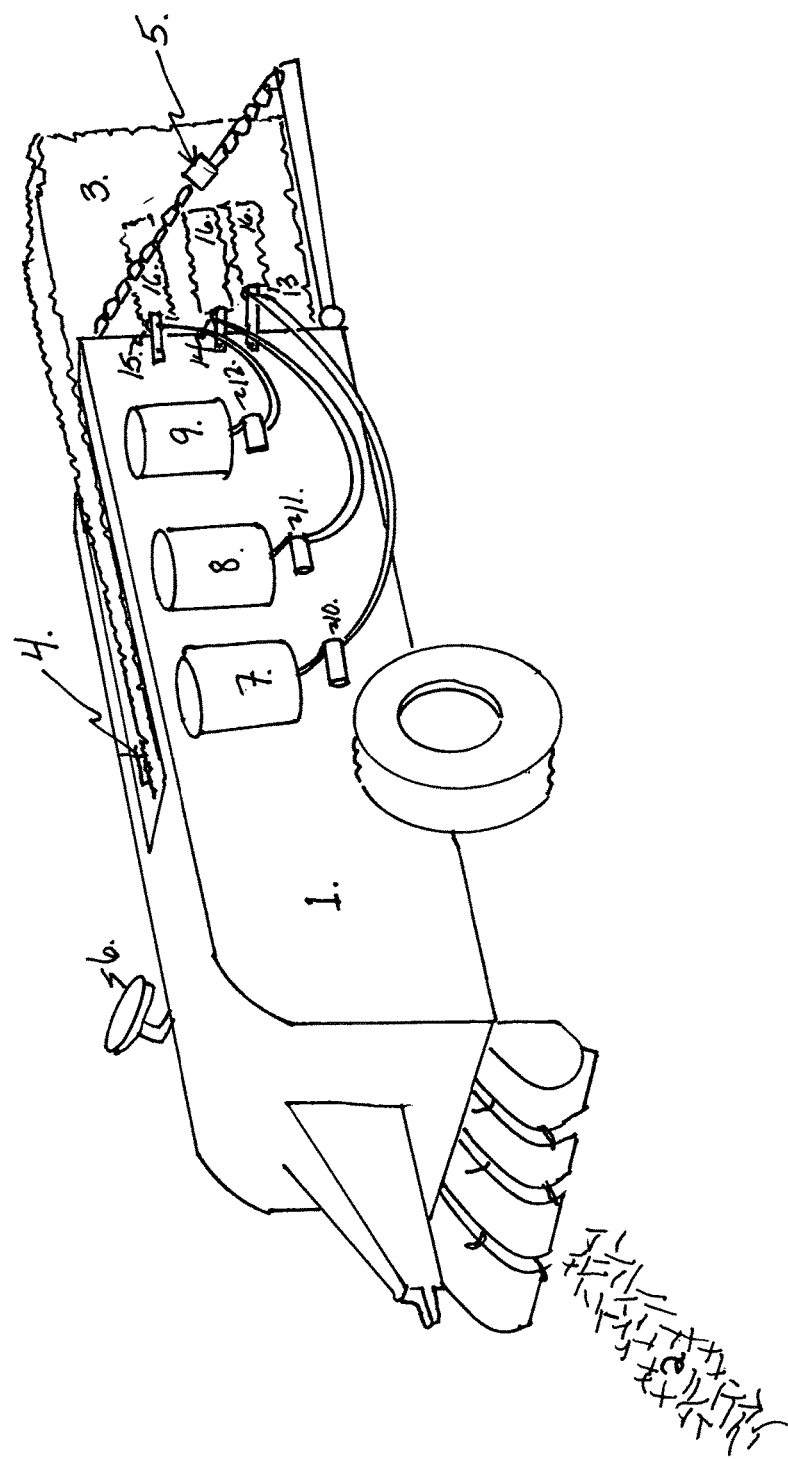
FIG. 1 is a view of a baler showing the relationship of the sensors and an embodiment of the invention using multiple marking devices.
Figure 2:
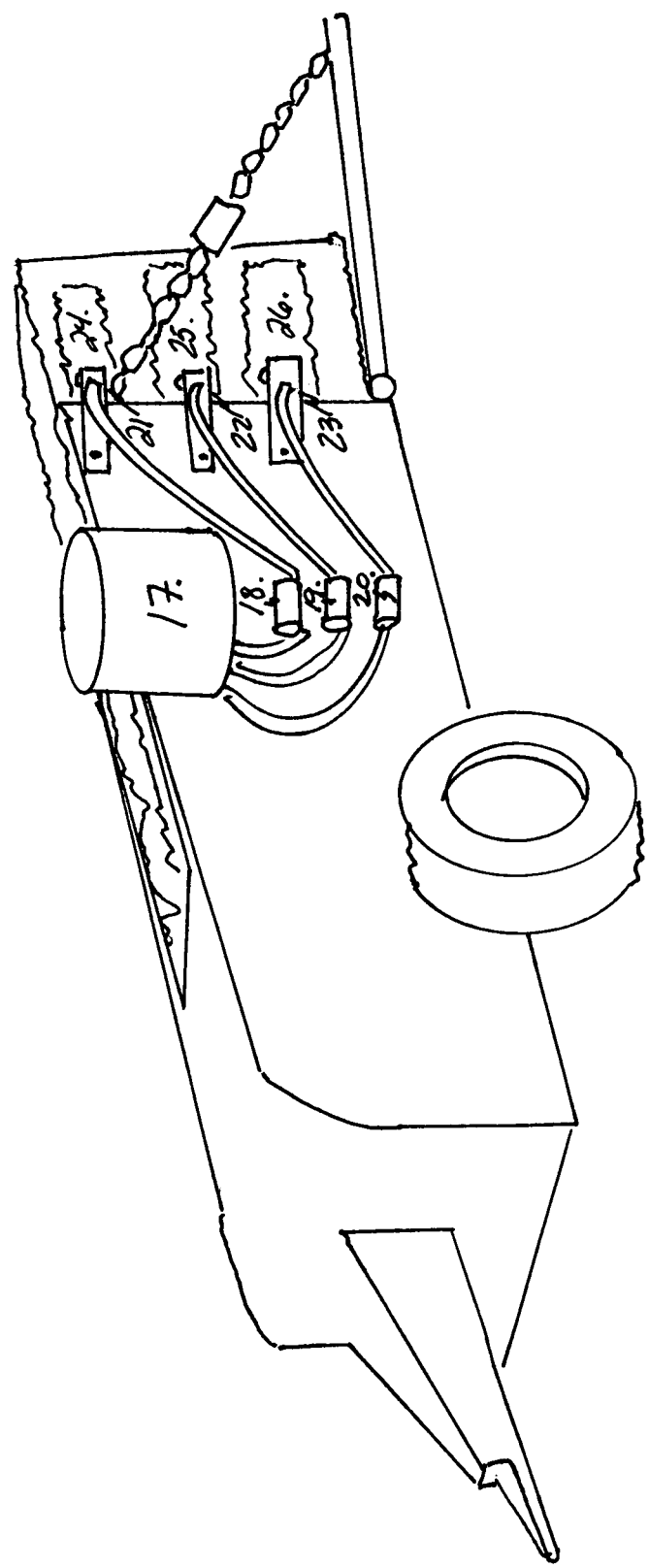
FIG. 2 is one embodiment using a single color marking with multiple application devises.

A baler 1 picks up loose hay from a windrow 2 and processes it as a compressed packaged bale 3. Sensors for moisture 4 typically read moisture in the compressed bale. Sensors for weight typically read the amount for each individual bale after it is completely formed which is at the rear of the baler which can be accomplished by reading one or more load cells 5. Sensors that read the position at which the bale is made are typically a GPS receiver 6. A baler may equipped with any or all of these sensors or with alternative sensors. When moisture sensors 4 and a weight sensor 5 are located on the baler, density of the bale can be calculated after adjusting the weight of the bale to 100% dry mater based on readings for the moisture sensors. The density of the bales which is the bale weight corrected to 100% dry matter divided by the cubic area has a strong correlation to the feed quality in an alfalfa bale as disclosed by Robert in A method for Calculating Feed Value of Alfalfa Hay Using Information Available at Time of Baling.

As these sensors collect values for the bales as they are formed, they can be sent to a processor. Looking at the values, the processor can group the values based on user inputs of ranges of values. As an example, if the input of moisture is a desired factor for grouping bales, the parameters of grouping could be as follows: all bales under 10% moisture designated as part of group 1; all bales between 10% and 15% moisture designated as part of group 2; all bales between 15% and 20% moisture designated part of group 3. Any other sensor input could be grouped in a similar fashion.

Based on grouping, bales will be marked by a device that is capable of applying differential marks to the exterior of the bale. In one embodiment, this device is a sprayer that is mounted in a position so that it can spray the outside of the bale. In this embodiment, the sprayer is equipped with multiple reservoirs 7, 8 and 9 each carrying a different color of dye used to mark the exterior of the bale. In this embodiment, each reservoir is equipped with its individual pump 10, 11 and 12. Each pump is then connected to a spray device 13, 14 and 15 which are arranged on the baler to spray on the exterior of the bale with a differential mark 16. As an example, reservoir 7 could have red dye and if the processor was set to group bales between 10% and 15% moisture, all bales within that range would have a red mark. In this example, if reservoir 8 had blue dye in it and the processor was set to group all bales between 15% and 20% as the second group, all bales within that range would have a blue mark. To further the example, if reservoir 9 had black dye in it and the processor was set to group all bales over 20% as a third group, all ales over 20% would have a black mark.

The processor has grouped readings from sensors according to user input ranges. The processor will output a signal to a designated pump 10, 11 and 12 for each group. The designed pump for the group will apply a spray mark on the exterior of the bale that is a distinct color or shape. As an example, reservoir 7 could have red dye and if the processor was set to group bales between 10% and 15% moisture, all bales within that range would have a red mark. In this example, if reservoir 8 had blue dye in it and the processor was set to group all bales between 15% and 20% as the second group, all bales within that range would have a blue mark. To further the example, if reservoir 9 had black dye in it and the processor was set to group all bales over 20% as a third group, all ales over 20% would have a black mark. Additionally a forth group could be distinguished by not having a mark.

In another embodiment of this invention, only one reservoir 17 is used with just one color of dye. The designated pumps 18, 19 and 20 are supplied from that individual reservoir. Each designated pump is connected to designated spray devices 21, 22 and 23. The processor groups the bales based on the selected values and controls which pump or combination of pumps should apply a mark to the bale. In the case. The marks are the same color, and bales are distinguished by the number of the same color or marks that are applied to the bale. As a matter of example, the first t group could have one mark 24, a second group could have 2 marks 24 and 25, and a third group could have three marks 24, 25 and 26. Additionally, a forth group could be distinguished by not having a mark.

in the case where multiple sensor inputs are used to calculate a further value such as using weight and moisture to calculate density to derive feed quality, the processor will perform the required calculations before grouping the bales. Moisture readings are taken from a sensor 4 and sent to the processor. Weight readings are taken from sensor 5 and sent to the processor. The processor then calculates a density by correcting the weight to 100% dry matter, and then dividing that weight by the cubic area of the bale to get a dry density of the bale. Based on values for dry density that have been input, the processor determines which variation of marking to apply to the bale thru spray devices 13, 14 and 15 or 21, 22 and 23.

What is claimed:

1. A hay baler which color marks hay bales for improved sorting and stacking, comprising
    at least one sensor for sensing a property of hay or a hay bale, the at least one sensor generating an output value based on the property of the hay or hay bale,
    a processor receiving the output value directly from the at least one sensor,
    a first marker controlled by the processor for selectively applying a first visual color mark to the exterior of a hay bale, the first marker including a first reservoir for containing a supply of dye having a first color, a first pump fluidically connected to the first reservoir and communicatively connected to the processor, and a first spray device fluidically connected to the first pump, the first spray device being disposed at a hay bale output of the baler to apply the first visual color mark to the exterior of the hay bale,
    at least one second marker controlled by the processor for selectively applying a second visual color mark to the exterior of the hay bale, the at least one second marker including a second reservoir containing a supply of dye having a second color which is different from the first color, a second pump fluidically connected to the second reservoir and communicatively connected to the processor, and a second spray device fluidically connected to the second pump, the second spray device being disposed at the hay bale output to apply the second visual color mark to the exterior of the hay bale,
    wherein the processor receives values output based on the properties of hay or a hay bale as it is baled from the at least one sensor, analyzes and groups, as each hay bale is baled, the values of those outputs based on multiple selected ranges and generates a marker output, as each bale is baled, the marker output activating the pump of one marker to spray and mark the outside of the hay bale with one color based on the group to which the hay bale belongs,
    whereby bales are grouped and color marked as they are being baled, and
    whereby bales baled by the hay baler may be immediately sorted and stacked based on color marks.

2. A hay baler as in claim 1, where the at least one sensor comprises a moisture sensor disposed on the baler between a windrow input and the hay bale output to measure moisture in hay before it is baled, the moisture sensor outputting moisture values to the processor.

3. A hay baler as in claim 1, where the at least one sensor comprises at least one load cell disposed on the baler at the hay bale output to measure hay bale weight, the at least one load cell outputting weight values to the processor.

4. A hay baler as in claim 1, where the at least one sensor comprises a GPS receiver disposed on the baler, which outputs global position values of the bale as it is finished being formed to the processor.

5. A hay baler as in claim 1, where the at least one sensor comprises: (a) a moisture sensor disposed on the baler between a windrow input and the hay bale output to measure moisture in hay before it is baled, the moisture sensor, and outputting moisture values to the processor, and (b) at least one load cell disposed on the baler at the hay bale output to measure hay bale weight, the at least one load cell outputting weight values to the processor, and wherein the processor adjusts the weight values to 100% dry matter and calculates a dry matter density value.

6. A hay baler which applies grouping marks to hay bales for sorting and stacking, comprising
    at least one sensor for sensing a property of hay or a hay bale, the at least one sensor generating an output value based on the property of the hay or hay bale,
    a processor receiving the output value directly from the at least one sensor,
    a reservoir for containing a supply of dye;
    a first marker controlled by the processor for selectively applying a first visual mark to the exterior of a hay bale, the first marker including a first pump fluidically connected to the reservoir and communicatively connected to the processor, and a first spray device fluidically connected to the first pump, the first spray device being arranged to apply the first visual mark to the exterior of the hay bale,
    at least one second marker controlled by the processor for selectively applying a second visual mark, which is different from the first visual mark, to the exterior of the hay bale, the at least one second marker including a second pump fluidically connected to the reservoir and communicatively connected to the processor, and a second spray device fluidically connected to the second pump, the second spray device being arranged to apply the second visual mark to the exterior of the hay bale,
    wherein the processor receives values output based on the properties of hay or hay bales as it is baled from the at least one sensor, analyzes and groups, as each hay bale is baled, the values of those outputs based on multiple selected ranges and generates a marker output, as each bale is baled, the marker output activating one or more of the multiple pumps to spray and mark the outside of the hay bale based on the group to which the hay bale belongs,
    whereby bales are grouped and differentially marked as they are being baled, and whereby bales baled by the hay baler may be immediately sorted and stacked based on differential marking.

7. A hay baler as in claim 6, where the at least one sensor comprises a moisture sensor disposed on the baler between a windrow input and the hay bale output to measure moisture in hay before it is baled, the moisture sensor outputting moisture values to the processor.

8. A hay baler as in claim 6, where the at least one sensor comprises at least one load cell disposed on the baler at the hay bale output to measure hay bale weight, the at least one load cell outputting weight values to the processor.

9. A hay baler as in claim 6, where the at least one sensor comprises a GPS receiver disposed on the baler, which outputs global position values of the bale as it is finished being formed to the processor.

10. A hay baler as in claim 6, where the at least one sensor comprises: (a) a moisture sensor disposed on the baler between the windrow input and the hay bale output to measure moisture in hay before it is baled, the moisture sensor, and outputting moisture values to the processor, and (b) at least one load cell disposed on the baler at the hay bale output to measure hay bale weight, the at least one load cell outputting weight values to the processor, and wherein the processor adjusts the weight values to 100% dry matter and calculates a dry matter density value.

* * * * *